(12) United States Patent
Payne, Jr.

(10) Patent No.: US 6,938,620 B2
(45) Date of Patent: Sep. 6, 2005

(54) HEADWEAR FOR USE BY A SLEEP APNEA PATIENT

(76) Inventor: Charles E. Payne, Jr., 4215 Alderwood La., Charlotte, NC (US) 28215

(*) Notice: Subject to any disclaimer, the term of this patent is extended or adjusted under 35 U.S.C. 154(b) by 83 days.

(21) Appl. No.: 10/215,927

(22) Filed: Aug. 9, 2002

(65) Prior Publication Data

US 2004/0025885 A1 Feb. 12, 2004

(51) Int. Cl.[7] ................................................ A61F 5/56
(52) U.S. Cl. ................... 128/848; 128/208.11; 128/857
(58) Field of Search ............................... 2/171, DIG. 6; 128/208.11, 208.17, 208.18, 857–858; 604/174, 179

(56) References Cited

U.S. PATENT DOCUMENTS

| | | | | |
|---|---|---|---|---|
| 4,665,566 A | * | 5/1987 | Garrow | ........................... 2/171 |
| 4,836,200 A | * | 6/1989 | Clark | ..................... 128/207.18 |
| 5,188,101 A | * | 2/1993 | Tumolo | .................. 128/207.18 |
| 5,217,294 A | * | 6/1993 | Liston | ......................... 362/105 |
| 5,682,881 A | | 11/1997 | Winthrop et al. | |
| 5,687,715 A | | 11/1997 | Landis et al. | |
| 5,724,965 A | | 3/1998 | Handke et al. | |
| 5,893,365 A | | 4/1999 | Anderson | |
| 6,019,101 A | | 2/2000 | Cotner et al. | |
| 6,044,844 A | | 4/2000 | Kwok et al. | |
| 6,105,575 A | | 8/2000 | Estes et al. | |
| 6,171,258 B1 | | 1/2001 | Karakasoglu et al. | |
| 6,192,886 B1 | | 2/2001 | Rudolph | |

\* cited by examiner

*Primary Examiner*—Michael A. Brown
(74) *Attorney, Agent, or Firm*—Schwartz Law Firm P.C.

(57) ABSTRACT

Headwear is adapted for use by a patient to position airway tubes of a nasal interface operatively connected to a positive airway pressure device. The headwear includes an elongated head strap for being worn around a head of the patient. First and second tube holders are attached to the head strap, and adapted for engaging and holding respective airway tubes of the nasal interface to retain the tubes in a desired position during use. Each of the tube holders includes an elastic strip extending along a longitudinal dimension of the head strap. The elastic strip cooperates with the head strap to form an eye for receiving an airway tube of the nasal interface.

9 Claims, 4 Drawing Sheets

HEADWEAR FOR USE BY A SLEEP APNEA PATIENT

TECHNICAL FIELD AND BACKGROUND OF INVENTION

This application relates to headwear for use by a sleep apnea patient. The invention serves to position airway tubes of a nasal interface operatively connected to a positive airway pressure device used in the treatment of sleep apnea. The invention is especially applicable for use with the NASAL-AIRE® interface sold by Innomed Technologies of Boca Raton, Fla. In alternative applications, the invention may be used in combination with any other medical device, such as that designed to provide mechanical respiration assistance in the treatment of congestive heart failure, emphysema, and other respiratory conditions.

Sleep apnea is a serious, potentially life-threatening breathing disorder characterized by brief interruptions of breathing during sleep. In a given night, the number of involuntary breathing pauses or "apneic events" may be as high as 20 to 30 or more per hour. These breathing pauses are almost always accompanied by snoring between apnea episodes, although not everyone who snores has this condition. Sleep apnea can also be characterized by choking sensations. The frequent interruptions of deep, restorative sleep often lead to early morning headaches and excessive daytime sleepiness.

Certain mechanical and structural problems in the airway cause the interruptions in breathing during sleep. In some people, apnea occurs when the throat muscles and tongue relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed. With a narrowed airway, the person continues his or her efforts to breathe, but air cannot easily flow into or out of the nose or mouth. Unknown to the person, this results in heavy snoring, periods of no breathing, and frequent arousals causing abrupt changes from deep sleep to light sleep.

During the apneic event, the person is unable to breathe in oxygen and to exhale carbon dioxide, resulting in low levels of oxygen and increased levels of carbon dioxide in the blood. The reduction in oxygen and increase in carbon dioxide alert the brain to resume breathing and cause an arousal. With each arousal, a signal is sent from the brain to the upper airway muscles to open the airway; breathing is resumed, often with a loud snort or gasp. Frequent arousals, although necessary for breathing to restart, prevent the patient from getting enough restorative, deep sleep.

The specific therapy for sleep apnea is tailored to the individual patient based on medical history, physical examination, and the results of polysomnography. Medications are generally not effective in the treatment of sleep apnea. Dental appliances that reposition the lower jaw and the tongue have been helpful to some patients with mild sleep apnea. Possible side effects include damage to teeth, soft tissues, and the jaw joint. Some patients with sleep apnea may need surgery. Although several surgical procedures are used to increase the size of the airway, none of them is completely successful or without risks. More than one procedure may need to be tried before the patient realizes any benefits.

Positive ventilation therapy is the most common effective treatment for sleep apnea. Nasal continuous positive airway pressure, or "CPAP", is the treatment of choice for most people with obstructive and mixed apnea. Hundreds of thousands of CPAP devices are currently available for treating sleep apnea. Bi-level positive airway pressure is a variation on CPAP. Instead of providing air at a constant, steady pressure all night, the machine "senses" how much air a person needs, based on inspiration and expiration, and varies its level of pressure accordingly. As a further alternative, several manufacturers have begun to offer a new generation of responsive or "smart" devices. These devices incorporate flow and pressure sensors and automatic regulation systems.

In each of the above treatment devices, a flexible hose or tubing provides a ventilation conduit interconnecting the device and an airway passage of the patient. According to one popular commercial product, the ventilation tubing is secured to the patient using a face mask and harness assembly worn on the head. This product is bulky, cumbersome, and generally uncomfortable to wear while sleeping.

The NASAL-AIRE® product by Innomed represents a substantial improvement over this prior art. The NASAL-AIRE® product utilizes a hollow under-nose reservoir which extends across the upper lip of the patient, and has two soft nasal insert sleeves for positioning in the nares of the nose. Flexible tubing connects to opposite ends of the nasal reservoir and conveniently drapes over the patient's ears to stabilize the reservoir under the nose. The opposite ends of the tubing are connected to a Y-shaped coupling. The coupling forms a single ventilation opening which connects to a main supply line of the treatment device. Using the NASAL-AIRE® product, the patient is free to talk, eat, drink, watch TV, and wear eyeglasses. While the product is especially designed and marketed for use without separate retaining means, the loose flexible tubing often becomes malpositioned and/or pinned between the patient's head and pillow during sleep. At a minimum, this can be an annoyance to the patient and in some cases may obstruct proper airflow to one or both nostrils.

SUMMARY OF INVENTION

Therefore, it is an object of the invention to provide headwear especially adapted for use by a sleep apnea patient.

It is another object of the invention to provide headwear for a sleep apnea patient which securely retains and positions airway tubes of the nasal interface during sleep while affording a wide range of pivoting adjustment of the airway tubes in a forward and rearward direction.

It is another object of the invention to provide headwear for a sleep apnea patient which is conveniently applied to and removed from the head.

It is another object of the invention to provide headwear for a sleep apnea patient which is lightweight and comfortable to wear.

It is another object of the invention to provide headwear for a sleep apnea patient which is relatively inexpensive to manufacture.

It is another object of the invention to provide headwear for a sleep apnea patient which includes multiple tube holders.

It is another object of the invention to provide headwear for a sleep apnea patient which does not cover the face of the patient.

It is another object of the invention to provide headwear for a sleep apnea patient which is adjustable to fit multiple size heads.

It is another object of the invention to provide an improved nasal interface which includes headwear for positioning the airway tubes on the patient.

It is another object of the invention to provide a method of positioning airway tubes of a nasal interface.

These and other objects of the present invention are achieved in the preferred embodiments disclosed below by providing headwear adapted for use by a patient to position airway tubes of a nasal interface operatively connected to a positive airway pressure device. The headwear includes an elongated head strap for being worn around a head of the patient. First and second tube holders are attached to the head strap, and adapted for engaging and holding respective airway tubes of the nasal interface to retain the tubes in a desired position during use. Each of the tube holders includes an elastic strip extending along a longitudinal dimension of the head strap. The elastic strip cooperates with the head strap to form an eye for receiving an airway tube of the nasal interface.

Preferably, the head strap is constructed of a breathable neoprene material.

According to another preferred embodiment of the invention, the head strap has opposing first and second ends, and further includes means for releasably attaching the first and second ends together to secure the headwear on the head of the patient.

According to another preferred embodiment of the invention, the means for releasably attaching includes hook fasteners formed with one of the first and second ends of the head strap. The hook fasteners are adapted for releasably mating with a fabric surface on the other of the first and second ends of the head strap.

Alternatively, the ends of the head strap are permanently joined together to form a headband.

Preferably, the first and second tube holders are located on the head strap such that when the strap is positioned on the head of the patient, the first and second tube holders are spaced apart approximately 180 degrees.

In another embodiment, the invention is a combination headwear and nasal interface. The nasal interface is adapted for connection to a positive airway pressure device used by a patient. The nasal interface includes a plurality of airway tubes. The headwear positions the airway tubes on the patient. The headwear includes an elongated head strap for being worn around a head of the patient. First and second tube holders are attached to the head strap, and engage and hold respective airway tubes of the nasal interface to retain the tubes in a desired position during use. Each of the tube holders includes an elastic strip extending along a longitudinal dimension of the head strap. The elastic strip cooperates with the head strap to form an eye for receiving an airway tube of the nasal interface.

According to another preferred embodiment of the invention, the nasal interface further includes an under-nose reservoir adapted for positioning across an upper lip of the patient.

According to another preferred embodiment of the invention, the under-nose reservoir has first and second nasal insert sleeves adapted for positioning in respective nares of a nose of the patient.

According to another preferred embodiment of the invention, a Y-shaped coupling is connected to respective ends of the airway tubes, and defines a single ventilation opening adapted for connecting to a main ventilation supply line of the positive airway pressure device.

In yet another embodiment, the invention is a method of positioning a plurality of airway tubes of a nasal interface adapted for connecting to a positive airway pressure device used by a patient. The method includes the steps of applying an elongated head strap around a head of the patient. The airway tubes are retained in a desired fixed position using respective elastic strips. Each of the strips extends along a longitudinal dimension of the head strap, and cooperates with the head strap to form an eye for receiving an airway tube of the nasal interface.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
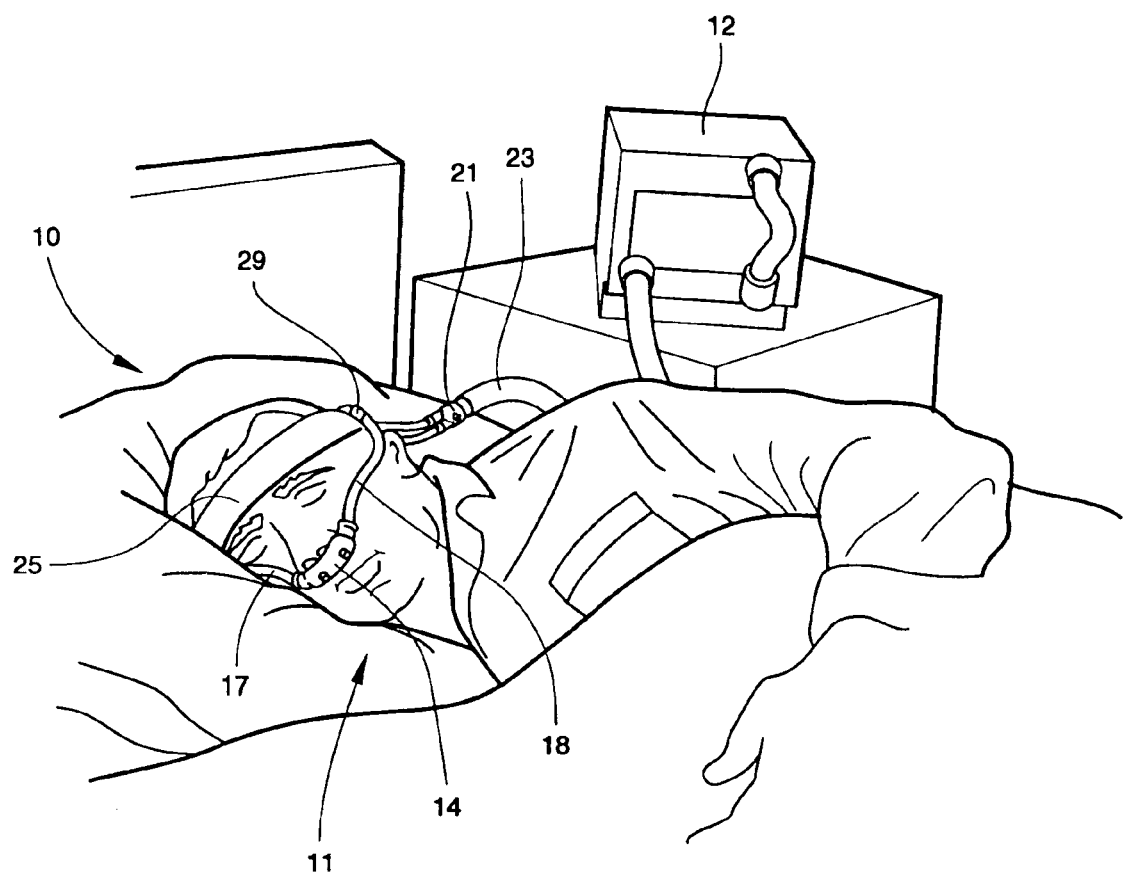
FIG. 1 is an environmental perspective view of the headwear according to one preferred embodiment of the invention, and showing the headwear worn by a sleep apnea patient to position the airway tubes of the nasal interface.

Referring now specifically to the drawings, headwear for a sleep apnea patient according to the present invention is illustrated in FIG. 1, and shown generally at reference numeral 10. The headwear 10 is especially applicable for use with a nasal interface 11, such as that sold under the trademark NASAL-AIRE®. The nasal interface 11 connects to a positive airway pressure device 12. One example of a positive airway pressure device 12 is described in U.S. Pat. No. 6,105,575 issued to Respironics, Inc. of Pittsburgh, Pa. The complete disclosure of this patent is incorporated herein by reference.

Figure 2:
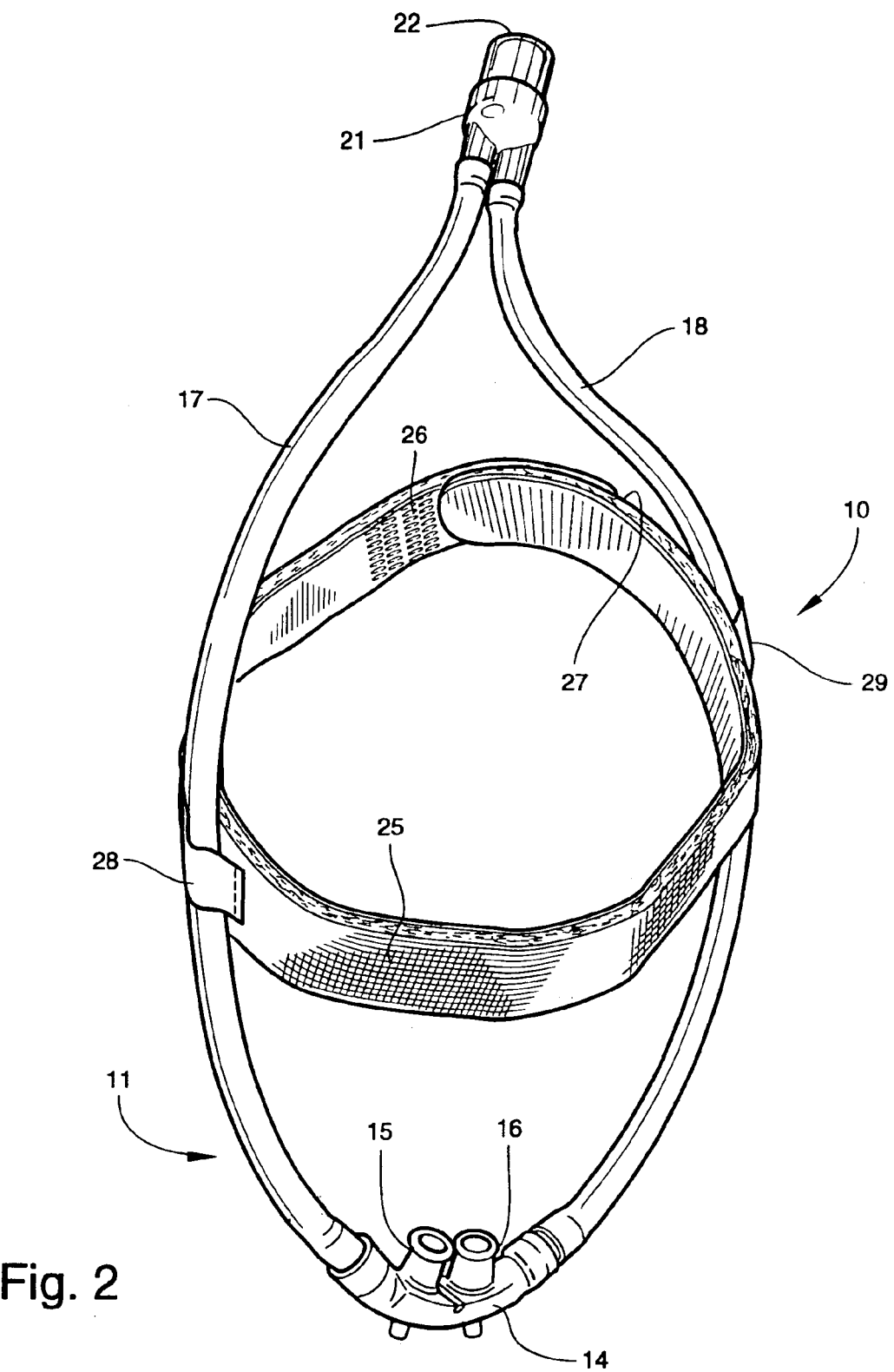
FIG. 2 is a perspective view of the headwear secured to the nasal interface, and showing the ends of the strap attached.

As shown in FIGS. 1 and 2, the nasal interface 11 includes a hollow under-nose reservoir 14 formed of a soft, flexible silicone elastomer. The under-nose reservoir 14 extends across the upper lip of the patient, and has two molded nasal insert sleeves 15 and 16 for positioning in the nares of the nose. Flexible rubber airway tubes 17 and 18 connect to opposite ends of the under-nose reservoir 14, and extend outwardly a distance sufficient to comfortably fit the interface 11 around the head of the patient. The opposite ends of the airway tubes 17, 18 are connected to a hollow Y-shaped coupling 21. The coupling 21 forms a single ventilation opening 22 which connects to a main supply line 23 of the treatment device 12.

Figure 3:
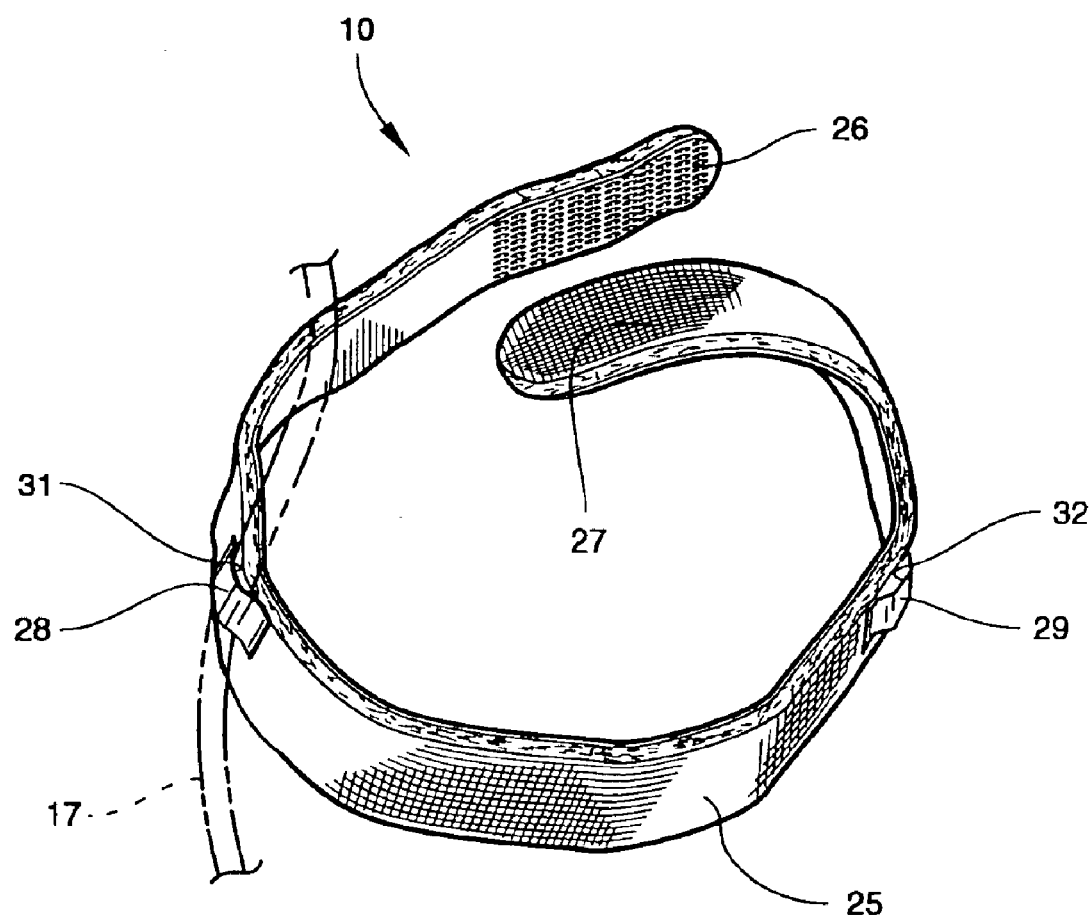
FIG. 3 is a perspective view of the headwear with the ends of the strap detached.

As best shown in FIGS. 2 and 3, the headwear 10 includes an elongated neoprene head strap 25 with a section of hook fasteners 26 at one end adapted to releasably mate with an outside fabric surface 27 of the strap 25 at an opposite end. The hook fasteners 26 and fabric surface 27 cooperate to provide an adjustable "touch" fastening system which securely holds the strap 25 to the head of the patient, and offers convenient size adjustment and added comfort. The neoprene rubber is soft, resilient, and breathable. The fabric is preferably a cotton or cotton blend material, and covers the entire outside surface of the head strap 25. In an alternative embodiment, the ends of the head strap 25 are permanently joined together to form an elastic headband.

Figure 4:
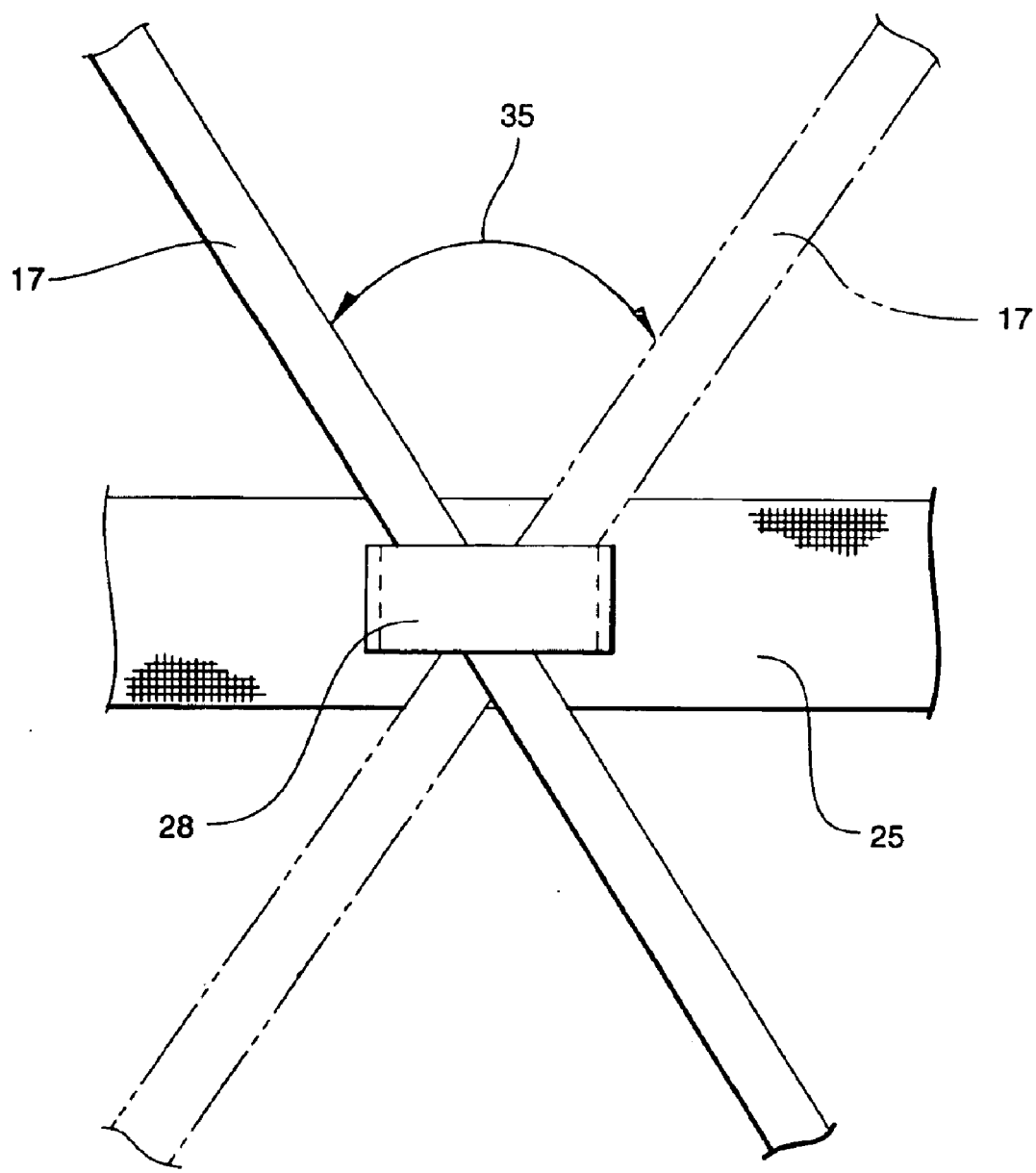
FIG. 4 is an enlarged fragmentary view of the headwear showing the angle of adjustment defined by the tube holder.

The head strap 25 has first and second tube holders 28 and 29 attached at respective holding points to retain the airway tubes 17, 18 of the nasal interface 11 in a desired position during use, and to stabilize the reservoir 14 under the nose of the patient. Each tube holder 28, 29 comprises a rectangular elastic strip having first and second opposing ends sewn to the head strap 25, and first and second opposing sides unattached to the head strap 25. The first and second sides extend parallel to a longitudinal dimension of the head strap 25, as best shown in FIG. 4. The elastic strips cooperate with the head strap 25 to form respective eyes 31 and 32 which are pulled open by the patient to receive the airway tubes 17, 18 of the nasal interface 11.

Each tube holder 28, 29 extends along a longitudinal dimension of the head strap 25, as best shown in FIG. 4, and defines a relatively wide adjustment zone which allows the airway tube 17,18 to pivot in a forward and rearward direction, as indicated at arrow 35, while frictionally resisting sliding movement through the holder 28, 29. Preferably the adjustment zone extends through an angle of approximately 60 degrees or more. The angle of adjustment defined by the tube holders 28, 29 creates a more comfortable and adjustable fit as the airway tubes 17, 18 extend from under the nose the patient to the head strap 25.

The nasal interface 11 is applied to the head strap 25 by detaching the Y-coupling 21 and sliding the ends of the airway tubes 17, 18 through the eyes of the tube holders 26, 27. When the strap 25 is properly positioned on the head of the patient, the tube holders 26, 27 are preferably spaced apart approximately 180 degrees. As the patient sleeps, the headwear 10 effectively positions the airway tubes 17, 18 on either side of the face promoting increased comfort and security, and reducing the likelihood of pinching and inadvertent disconnection of the tubes.

Headwear for a sleep apnea patient is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. In combination with a nasal interface adapted for connection to a positive airway pressure device used by a patient, said nasal interface comprising a plurality of airway tubes, the improvement comprising headwear for positioning said airway tubes on the patient, said headwear comprising:
   (a) an elongated head strap for being worn around a head of the patient; and
   (b) first and second tube holders attached to said head strap and engaging and holding respective airway tubes of the nasal interface to retain the tubes in a desired position during use, each of said tube holders comprising a rectangular elastic strip having first and second opposing ends fixedly attached to said head strap and first and second opposing sides unattached to said head strap, said first and second sides extending parallel to a longitudinal dimension of said head strap, and cooperating with said head strap to form an eye for receiving an airway tube of the nasal interface, whereby said elastic strip defines an adjustment zone which allows the airway tube to pivot in a forward and rearward direction while frictionally resisting sliding movement of the airway tube through said tube holder.

2. A combination according to claim 1, wherein said head strap comprises neoprene.

3. A combination according to claim 1, wherein said head strap has opposing first and second ends, and comprises means for releasably attaching said first and second ends together to secure said headwear on the head of the patient.

4. A combination according to claim 3, wherein said means for releasably attaching comprises hook fasteners formed with one of the first and second ends of said head strap and adapted for releasably mating with a fabric surface on the other of the first and second ends of said head strap.

5. A combination according to claim 1, wherein said first and second tube holders are located on said head strap such that when said strap is positioned on the head of the patient, said first and second tube holders are spaced apart approximately 180 degrees.

6. A combination according to claim 1, wherein said nasal interface further comprises an under-nose reservoir adapted for positioning across an upper lip of the patient.

7. A combination according to claim 6, wherein said under-nose reservoir comprises first and second nasal insert sleeves adapted for positioning in respective nares of a nose of the patient.

8. A combination according to claim 1, and comprising a Y-shaped coupling connected to respective ends of said airway tubes, and defining a single ventilation opening adapted for connecting to a main ventilation supply line of the positive airway pressure device.

9. A method of positioning a plurality of airway tubes of a nasal interface adapted for connecting to a positive airway pressure device used by a patient, said method comprising the steps of:
   (a) applying an elongated head strap around a head of the patient;
   (b) retaining the airway tubes in a desired fixed position using respective rectangular elastic strips, each of the strips having first and second opposing ends fixedly attached to the head strap and first and second opposing sides unattached to the head strap, the first and second sides extending parallel to a longitudinal dimension of the head strap, and cooperating with the head strap to form an eye for receiving an airway tube of the nasal interface, whereby each elastic strip defines an adjustment zone which allows the airway tube to pivot in a forward and rearward direction while frictionally resisting sliding movement of the airway tube through the elastic strip.

\* \* \* \* \*